(12) United States Patent
Willuweit et al.

(10) Patent No.: US 7,384,777 B2
(45) Date of Patent: Jun. 10, 2008

(54) MICROBIOLOGICAL CULTURE FOR TRIGGERING MICROBIOLOGICAL PROCESSES IN WATER

(75) Inventors: Thomas Willuweit, Hof (DE); Peter Söll, Hof (DE); Robert Müller, Hof (DE)

(73) Assignee: Söll Holding GmbH, Fischbachau (DE)

(*) Notice: Subject to any disclaimer, the term of this patent is extended or adjusted under 35 U.S.C. 154(b) by 239 days.

(21) Appl. No.: 10/381,259

(22) PCT Filed: Sep. 25, 2001

(86) PCT No.: PCT/EP01/11090

§ 371 (c)(1),
(2), (4) Date: Mar. 24, 2003

(87) PCT Pub. No.: WO02/24583

PCT Pub. Date: Mar. 28, 2002

(65) Prior Publication Data

US 2004/0101944 A1    May 27, 2004

(30) Foreign Application Priority Data

Sep. 25, 2000    (DE) ............................. 100 47 709

(51) Int. Cl.
C02F 3/34    (2006.01)
(52) U.S. Cl. .................................................. 435/262
(58) Field of Classification Search ................ 435/262; 119/231
See application file for complete search history.

(56) References Cited

U.S. PATENT DOCUMENTS

| | | | | |
|---|---|---|---|---|
| 4,996,150 A | * | 2/1991 | Joung et al. ................ 435/161 |
| 5,569,634 A | * | 10/1996 | Miller et al. .................. 502/64 |
| 5,679,364 A | * | 10/1997 | Levy ............................ 424/405 |
| 5,821,112 A | * | 10/1998 | Botto et al. .................. 435/262 |
| 6,153,416 A | | 11/2000 | Yuan ........................... 435/178 |
| 6,939,708 B2 | * | 9/2005 | Morris et al. ................ 435/262 |

FOREIGN PATENT DOCUMENTS

WO    WO 93/01138    1/1993

OTHER PUBLICATIONS

Merriam-Webster online Dictionary, 2005 Merriam-Webster, Inc., The word "Immobilize"—see attached sheet.*
The composition of Tryptic Soy Broth. (http://www.emdchemicals.com/)-see attached sheet and references therein(1995).*
The term "artificial" Merriam-Webster Online Dictionary—see at the web: http://www.m-w.com. p. 1 (Accessed on 2006).*
Zart D. & Bock E. High rate of aerobic nitrification and denitrification by *Nitrosomonas eutropha* grown in a fermentor with complete biomass retention in the presence of gaseous NO2 or NO, Arch, Microbiol., 1998, 169: 282-286, entire document.*
Holger Daims; Population Structure and Functional Analysis, by In Situ Techniques of Nitrifying Bacteria in Wastewater Treatment Plants; Dissertation Technische Universität München, 2001; p. 52.
Andreas Schramm et al.; Identification and Activities in Situ of *Nitrosospira* and *Nitrosopira* spp. as Dominant Populations in a Nitrifying Fluidized Bed Reactor; Appl. Environ. Microbiol. vol. 64, No. 9, pp. 3480-3485 (Jul. 1998).
Konrad Egli et al.; Community Analysis of Ammonia and Nitrite Oxidizers during Start-Up of Nitration Reactors; Applied and Environmental Microbiology, Jun. 2003, pp. 3213-3222.
Timothy A. Hovanec et al.; Comparative Analysis of Nitrifying Bacteria Associated with Freshwater and Marine Aquaria; Appl. Environ. Microbiol. vol. 62, No. 8, pp. 2888-2896) (1996).
W. Tappe et al.; Maintenance Energy Demand and Starvation Recovery Dynamics of *Nitrosomonas europaea* and *Nitrobacter winogradskyi* Cultivated in a Retentostat with Complete Biomass Retention;Appl. Environ. Microbiol. vol. 65, No. 6, pp. 2471-2477 (1999).

* cited by examiner

*Primary Examiner*—Sandra E. Saucier
*Assistant Examiner*—Satyendra K. Singh
(74) *Attorney, Agent, or Firm*—Nixon & Vanderhye P.C.

(57) ABSTRACT

A microbiological culture for triggering microbiological processes in bodies of water, soils, sediments, and/or muds contains chemo-lithoautotrophic bacteria that are immobilized. The bacteria are immobilized in a matrix having the form of capsules, gels, or gel spheres. The matrix material is selected from a wide range of natural and synthetic polymers.

23 Claims, 1 Drawing Sheet

MICROBIOLOGICAL CULTURE FOR TRIGGERING MICROBIOLOGICAL PROCESSES IN WATER

BACKGROUND OF THE INVENTION

The present invention relates to a microbiological culture for triggering microbiological processes in bodies of water, soils, sediments and/or muds by using living chemo-lithoautotrophic bacteria; the use of this culture for removing harmful substances, such as nitrogen compounds and/or phosphate, from bodies of water and/or from the air; a method for cleaning and/or treating water and/or soils by using the microbiological cultures; as well as a kid-of-parts, comprising immobilized microorganisms as well as a container for receiving and for metered dispensing of the microorganisms under life-supporting conditions.

Standing and flowing natural bodies of water have in general a certain self-cleaning power, i.e., contaminations can be decomposed to a limited extent. This self-cleaning power, however, is often insufficient in the case of greatly contaminated bodies of water. Microorganisms, which, in particular, can convert harmful nitrogen compounds into innocuous compounds such as elementary nitrogen, are often added to these bodies of water for enhancing the (self)-cleaning action.

The added microorganisms serve for triggering and enhancing, or taking over, the already present self-cleaning power in natural bodies of water and aquatic systems.

The microorganisms can be used in the form of cell suspensions and in this form, optionally in an aqueous solvent, can be introduced into the bodies of water. Also, the use of microorganisms in powder form is possible. In these preparations, the microorganisms are initially transformed into so-called permanent forms, such as spores, or they are lyophilized. As a result of the current within the body of water and because of diffusion, the microorganisms do not stay put but reach also other regions of the body of water. In these regions, the living conditions for the microorganisms can be unfavorable so that removal of contamination does not occur. Moreover, a fixation of the microorganisms in specially loaded water regions of the bodies of water is not possible.

In the field of aquarium technology, problems occur already for minimal amounts of soluble nitrogen compounds, because, for example, ammonia is toxic for fishes already in concentrations of 0.01 mg/l. In particular, in aquariums, which are artificial systems, the self-cleaning process is particularly susceptible to failure already for minimal amounts of foreign substances, such as nitrogen compounds or the like, contained therein.

In particular, when in the bodies of water to be treated hardly any active microorganisms are present, active microorganisms must be added in sufficiently high active concentrations in order to activate the self-cleaning powers of the bodies of water. For the operators of garden ponds and small bodies of water, microorganisms used for improving the water quality are obtainable in general in the form of so-called permanent forms or in lyophilized form. For larger bodies of water, the use of cell suspensions is preferable. It is also known to use microorganisms in encapsulated form.

The cell suspensions known in the prior art and also the microcapsules containing microorganisms usually do not employ chemo-autotrophic microorganisms in defined communities of species. Also, they have the disadvantage that the preparations can be stored only for a very short period of time, and the microorganisms will die off already after one or two days. Such formulations are thus not suitable for commerce.

When microorganisms are to be used for inoculation of bodies of water in order to activate their self-cleaning powers, the employed microorganisms must be present in very high concentration.

For the stabilization of the nitrogen cycle, the microbiological processes, such as nitrogen fixation, nitrogen assimilation, and denitrification generally present no problem; the degradation efficiency of nitrification processes and also the mineralization of organic nitrogen compounds are often insufficient.

In many microbiological processes it is a disadvantage that the duration of activity of the microorganisms is only a few days and then they die off. Moreover, many microorganisms do not form spores and can thus not be transformed into a permanent form, for example, they can be lyophilized only with loss of their activity. These microorganisms must be used in the vegetative form which means, in turn, that they must be stored under life-supporting conditions.

SUMMARY OF THE INVENTION

The present invention has the object to provide microbiological startup cultures which can be stored for a certain amount of time and which are suitable for triggering microbiological processes in an aquatic system and thus initiate the self-cleaning power of the system. A further object of the invention is to provide a method employing microorganisms which makes it possible to clean standing and/or flowing bodies of water at a fixed and predetermined location, i.e., to decompose the harmful substances by employing microorganisms.

The subject matter of the present invention is accordingly a microbiological culture for triggering microbiological processes in bodies of water, soils, sediments, and/or muds by using living chemo-lithoautotrophic bacteria characterized in that the bacteria are immobilized.

The term immobilized means in the context of the present invention that the bacteria, in the following referred to also as microorganisms, are not used in the form of cell suspensions or cell solutions as such but are surrounded by a matrix material and/or are applied onto it, wherein life-supporting conditions are observed. The immobilized bacteria are referred to in the following also as immobilisates.

Surprisingly, it was found that the bacteria cultures according to the invention in the immobilized form are well suited for triggering microbiological processes in bodies of water and in soils, and the cleaning processes in these systems can be significantly accelerated in this way. Moisture or water contained in the system to be cleaned comes into contact with the microorganisms, and contact between the harmful substances and the microorganisms also takes places in this way with decomposition of these substances. The starter culture according to the invention is suitable in particular for decomposition of organic and inorganic nitrogen compounds.

A further advantage of immobilization of the microorganisms resides in that they can be supplied with fresh medium, with nutrients and oxygen while being stored and can thus be protected against loss of activity. Moreover, it is possible to store the microorganisms even over an extended period of time so they must not be used immediately after their manufacture, as is the case in the systems known in the prior art.

The bodies of water and soils in which the bacteria cultures according to the invention can be used include all water-containing and moisture-containing systems. Bodies of water in the context of the present invention are natural and artificial, standing and flowing bodies of water, such as ponds and lakes, water treatment plants, aquariums, water of water circulation systems of industrial facilities and domestic facilities, or the like. The soils include the earth as a base on land and in water as well as sediments and muds, wherein, depending on the water contents, the transition between bodies of water and sediments is fluid.

The bacteria cultures according to the invention are suitable in particular for improving the cleaning efficiency of aquatic systems, such as aquariums, ponds, lakes, and water treatment plants.

DESCRIPTION OF PREFERRED EMBODIMENTS

Figure 1:
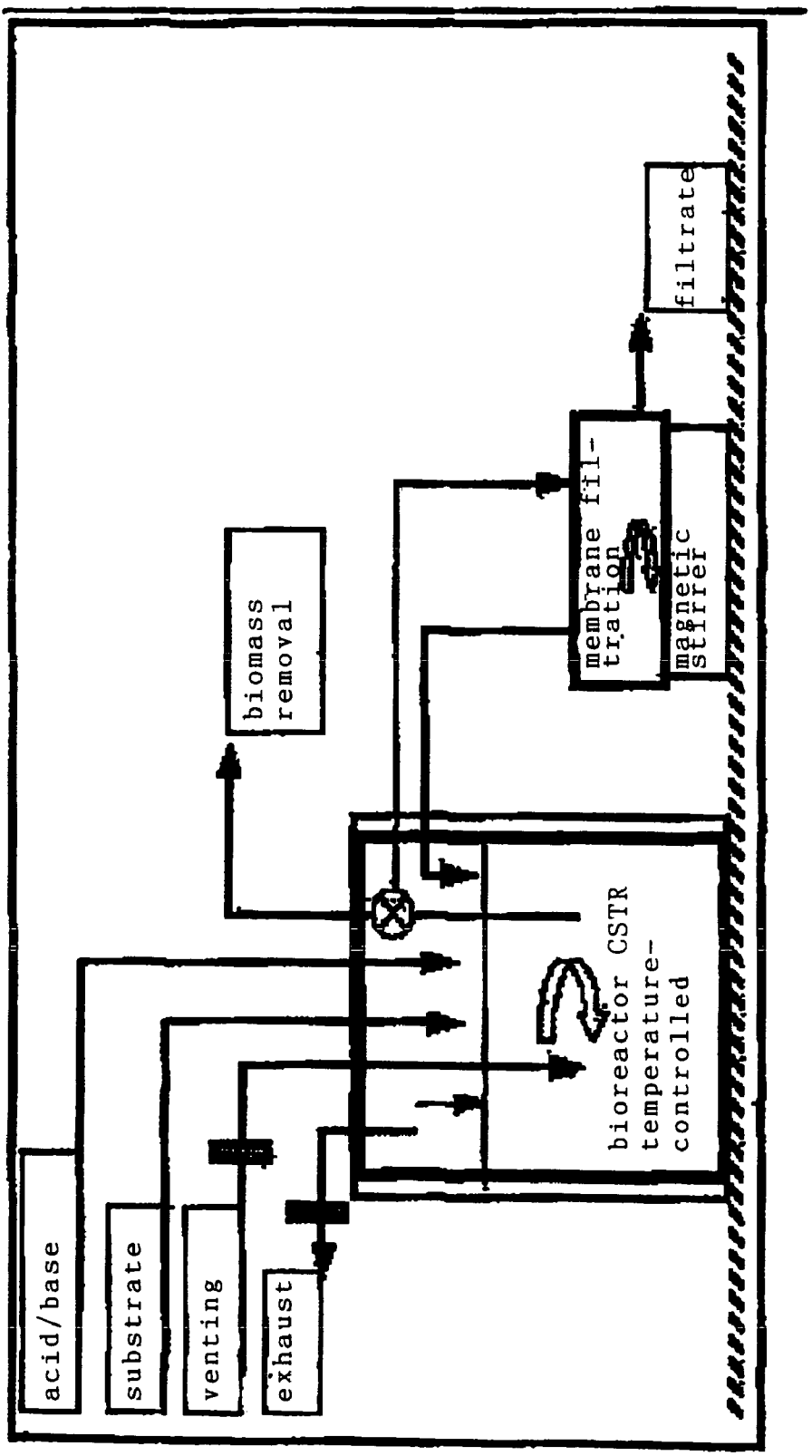
FIG. 1 shows schematically a bioreactor with biomass return suitable for culturing microorganisms to be employed in the present invention.

The microorganisms are preferably immobilized in a matrix wherein capsules, gels and/or gel spheres as a matrix form have been found to be particularly suitable. This type of immobilization has the advantage that moisture or water contained in the system to be cleaned can penetrate, by way of the net structure present within the capsule material or the gel material or by way of diffusion, into the immobilisate and can thus come into contact with the microorganisms. Via the capsule wall or the gel, preferably permeable for water and/or microorganisms, the microorganisms are simultaneously also dispensed into the surroundings so that outside of the capsules a contact between the harmful substances and the microorganisms can take place with decomposition of these substances.

The preferably employed capsules or spheres have preferably a diameter of approximately 100 to approximately 10,000 µm, in particular, of 100 to 5,000 µm, wherein the microorganisms, in a solid or a liquid form, are enveloped by, penetrated by and/or applied onto a solid to gel-like, in general polymeric, preferably porous polymer material.

By means of proper selection of the materials for the capsules/spheres, for example, natural or synthetic polymers, the capsules/spheres can be designed such that the bacteria and the substrate to be cleaned (water) can come into contact with one another. A possibly present capsule wall can be seal-tight, permeable, or semipermeable. The material of the capsules/spheres can also be of a multi-layer structure, i.e., one or several materials can be used. Accordingly, there is a plethora of possibilities for releasing the immobilized substance in a controlled fashion, for example, by destruction of the envelope or by permeation or also by chemical reactions which occur in the interior of the microcapsules.

In a preferred configuration of the present invention, the capsule wall is permeable for water and substances dissolved therein. In this embodiment, the contact of the harmful substances with the microorganisms is realized such that the water penetrates through the surface into the spheres and the cleaning processes take place in the interior. By means of the cleaning process, the microorganisms multiply until the holding capacity of the capsules/spheres or the gel has been reached and the wall bursts, i.e., the microorganisms are released.

For producing the immobilized microorganisms, natural or synthetic polymers can be used as the matrix materials.

In a preferred embodiment, gel-forming polymers and/or such polymers which are suitable for manufacturing the preferred forms such as capsules, spheres and/or gels are used. This has the advantage that bacteria can be received or embedded within the gel structure. Preferably, the materials should have such a strength and wear resistance that the immobilized microorganisms can be stored in this form under so-called life-supporting conditions, i.e., with addition of substrate and oxygen.

In a preferred embodiment such materials are used which dissolve or decompose slowly, preferably at a defined rate, in water so that slowly a release of microorganisms over a defined period of time takes place.

Moreover, polymers are preferred which optionally can also serve as a carbon source for the employed microorganisms. In this embodiment, the matrix is decomposed and degraded by the microorganisms. As soon as the structure has sufficiently large pores, a release of the microorganisms occurs.

Examples for suitable polymers are polymeric polysaccharides such as agar-agar or cellulose, proteins such as gelatin, gum arabic, albumin or fibrinogen, ethyl cellulose, methylcellulose, carboxy methyl ethyl cellulose, cellulose acetate, alkali cellulose sulfate, polyanilline, polypyrrole, polyvinyl pyrolidone, polystyrene, polyvinyl chloride, polyvinyl alcohol, polyethylene, polypropylene, copolymers of polystyrene and maleic acid anhydride, epoxy resins, polyethylene imines, copolymers of styrene and methyl methacrylate, polystyrene sulfonate, polyacrylate and poly methacrylate, polycarbonate, polyester, silicones, methylcellulose, mixtures of gelatin and water glass, gelatin and polyphosphate, cellulose acetate and phthalate, gelatin and copolymers of maleic acid anhydride and methyl vinyl ether, cellulose acetate butyrate, chitosan, poly dialkyl dimethyl ammonium chlorides, mixtures of poly acrylic acids and poly diallyl dimethyl ammonium chlorides, as well as any suitable mixtures of the above.

The polymer material can optionally be crosslinked. Conventional cross-linking agents are glutaraldehyde, urea/formaldehyde resins, tannin compounds such as tannic acid, alkali earth ions such as $Ca^{2+}$ ions which can be added, for example, in the form of chlorides, and their mixtures.

In a specially preferred embodiment, the alginates and alginate derivatives are used as matrix material. The alginates have the advantage that they have no negative effect on the activity of microorganisms and, moreover, they can be slowly decomposed by microorganisms over a certain period of time, such as a week up to several months. The slow decomposition of the matrix releases gradually the enclosed microorganisms in increasing quantities. From the biological decomposition of the wall material there results the further advantage that no residual materials or waste products remain in the body of water. When the immobilized bacteria cultures are placed, for example, in a corresponding container or a device for receiving and storing them, for example, a filter, into the medium to be treated, the filter can be refilled with the microorganisms according to the invention after dissolution of the employed immobilized microorganisms.

When the matrix material is present in the form of a capsule or sphere, the wall in a further preferred embodiment has a multi-layer configuration wherein gel-forming polymers and non-gel-forming polymers, preferably film-forming polymers, can be combined for the outer wall. In a preferred embodiment, alginates or alginate derivatives are selected as the gel-forming materials, and polymers are selected from cellulose derivatives, in particular, sodium cellulose sulfate, poly dialkyl dimethyl ammonium chlorides and/or polyethylene imines, as the further, preferably film-forming, materials. The polymer materials which are used in addition to the alginates or alginate derivatives form preferably the outer capsule wall. It was found that by employing an outer capsule material, selected from the aforementioned polymers, the wear resistance of the microcapsules and thus the shelf life was significantly improved.

In an especially preferred embodiment, purified alginates, in particular those alginates described under the CAS numbers 9005-38-3 and 9005-32-7, are used as gel-forming materials. The purified alginates have the advantage that they contain only a minimal amount of free organic substances which could possibly impair the stability and activity of the microorganisms. The employed alginates have preferably a high contents of L-guluron acid units.

In a further preferred embodiment, phyllosilicates or tectosilicates, preferably zeolites, are added to the alginate. The silicates stabilize with their mesh structures the gel material and slow the decomposition process of the alginate while, at the same time, they absorb ammonia and calcium on the mineral components of the sphere matrix.

The employed zeolites are comprised of more than 70% of clinoptilotith with inert by-minerals such as quartz. The particles size of the mineral admixtures is smaller than 600 μm. The added amount is 0.5 to 50% by weight of the employed dry substance of alginate. Preferably, 5-30% by weight of minerals, especially preferred weight (zeolite) =15-30% relative to 70-85% alginate, are used.

The microorganisms can be any suitable microorganisms for treating water, including marine type microorganisms, algaes and fungi. Preferably, the microorganisms are select-from chemo-lithoautotrophic nitrification microorganisms, such as ammonia oxidizing microorganisms and nitrite oxidizing microorganisms, which can be selected from the nitrification microorganisms, in particular, bacteria of the genus *Nitrosomonas, Nitrosococcus, Nitrosospira, Nitrosovibrio*, and *Nitrosospira*, in particular, the species *Nitrosomonas halophilia, Nitrosomonas eutropha*, and *Nitrosomonas europaea, Nitrosomonas oligotropha, Nitrosomonas ureae, Nitrosomonas aestuarii, Nitrosomonas marina, Nitrosomonas*, sp. 3 Nm 51, *Nitrosomonas communis, Nitrosomonas nitrosa, Nitrosomonas* sp. 1 Nm 33, *Nitrosomonas* sp. 2 Nm 41, *Nitrosomonas cryotolerans*, as well as nitrite-oxidizing bacteria of the genus *Nitrobacter* and *Nitrospira*, in particular, *Nitrobacter winogradskyi*.

Suitable are also heterotrophic nitrification organisms such as fungi of the genus *Aspergillus, Penicillium*, and *Cephalosporium*, algaes, *Arthrobacter* sp., *Alcaligenes faecilis, Nocordia* sp. as well as heterotrophic denitrification microorganisms such as *Paracoccus* sp., in particular, *Paracoccus pantothrophas* and *Pseudomonas* sp. It is also possible to employ any suitable combination, i.e., mixed cultures, of the microorganisms. The use of mixed cultures can provide a synergistic effect with respect to the activity and decomposition efficiency. Examples of mixed cultures are, for example, combinations of the species *Nitrosomonas* and *Nitrobacter* as well as optionally heterotrophic microorganisms.

In an especially preferred embodiment, species communities of different bacteria are used for cleaning and treating bodies of water, soils, etc., for example, for the decomposition of organic and inorganic nitrogen compounds. The employed species can first be cultured according to their special culturing conditions in a pure culture and subsequently can be immobilized. Culturing of bacteria in a pure culture makes it possible to provide a combination of basically any suitable species community in almost any suitable species ratio. An example for an especially preferred species community in the immobilisate is comprised of a) ammonia oxidizing (for example, Nitrosomonas) and b) nitrite-oxidizing (for example, Nitrobacter) and optionally c) nitrate-reducing and nitrite-reducing bacteria (for example, Paracoccus). It was found to be beneficial when the species ratio of the cell numbers in the immobilisate is preferably in the range of a:b of 1:10,000 to 1:1 and, particularly preferred, of 1:10,000 to 1:10 and when the species ratio of the b:c is preferably between 1,000:1 to 1:1, and especially preferred between 100:1 to 5:1.

Depending on the type of application, a person skilled in the art, based on his knowledge of the field, and optionally after performing tests or by using computer simulations, can determine the corresponding species and their ratios relative to one another.

In order to be able to microbiologically start a system in a short period of time, it was found to be expedient when the starter culture is added in a sufficiently high concentration.

For producing the immobilized bacteria according to the invention, conventionally cell suspensions are first cultured in a concentration of $1 \times 10^6$ to $5 \times 10^9$ cells per ml in a pure culture. In order to obtain microorganisms in a concentration as high as possible within the microcapsule, the obtained cell suspensions are subsequently concentrated preferably to $5 \times 10^8$ to $6 \times 10^9$ cells per ml. The concentration can be realized by conventional filtration methods known in the art.

Particularly when nitrifying microorganisms are immobilized, it was found to be especially expedient to use the microorganisms in the form of aqueous cell suspensions. In a preferred embodiment, stabilized microorganisms are used, in particular, such microorganisms according to the culturing process and stabilization in accordance with German patent application 199 08 109.3-41 with addition of NO and/or $NO_2$.

A particularly excellent stabilization of the microorganisms can be achieved when they are used as a cell suspension which contains a buffer system. Examples of suitable buffers are acetic acid/acetate, $HCO_3^-/CO_3^{2-}$, phosphoric acid/$H_2PO_3^-/HPO_3^{2-}$, citric acid/citrate, lactic acid/lactate, solid $CaCO_3$.

In order to reach an activity optimum of the microorganisms, the pH value in the gel capsules is preferably between 4 and 9, particularly preferred between 5 and 8 and, in particular, between 6.5 and 8.5. If adjustable under the application conditions, the starting cultures according to the invention are preferably carried out in a temperature range of a 8° C. to 35° C., in particular preferred in a range of 15° C. to 30° C., and more particularly between 20° C. and 30° C.

In another embodiment, the capsule core and/or the capsule wall contains pigments, for example, inorganic or organic white, black or color pigments and/or UV radiation filters. By employing pigments, it is possible, on the one hand, to impart to the capsules a pleasing appearance, and, on the other hand, the pigments can protect in particular light-sensitive microorganisms against too strong light and sun radiation. A further protection for harmful light action is provided by UV radiation filters. The pigments and/or the UV radiation filters can be immobilized, for example, together with the microorganisms and can be present within the core or can also be embedded in the capsule wall. This embodiment also includes the situation that the components are contained in the capsule interior in the matrix as well as in the capsule wall.

As pigments any suitable inorganic or organic pigments can be used which have no negative effect on the activity of the microorganisms. Examples of inorganic pigments are: lime ($CaCO_3$), titanium dioxide, lead white, zinc white, lithopone, antimony white, carbon black, iron oxide black, manganese black, cobalt black, antimony black, lead chromate, lead oxide read, zinc yellow, zinc green, cadmium red, cobalt blue, Prussian Blue, ultramarine blue, manganese purple, cadmium yellow, Schweinfurt green, molybdenum orange and molybdenum red, chromium orange and chromium red, chromium oxide green, strontium yellow etc. or naturally occurring pigments such as ocher, umber, green earth, terra-sienna, graphite, etc. Lime or $CaCO_3$ was found to be particularly suitable because it provides an additional buffering function and can also serve as a $CO_2$ source for the microorganisms.

The manufacture of the microcapsules can be realized in a known way by encapsulation of cell suspensions or solutions.

When microcapsules are to be prepared with several different microorganisms, the cell suspensions/solutions, as soon as the desired cell concentration has been adjusted, are mixed in the desired quantity ratios with one another and subsequently are immobilized as is known in the art. Suitable methods for immobilization of microorganisms are the micro encapsulation methods known in the prior art.

Examples for possible manufacturing processes are phase separation methods, also called coacervation, mechanical-physical methods, boundary layer polymerization as well as adsorptive methods.

Phase separation means that a dissolved polymer is transformed into a polymer-rich still solvent-containing phase by means of removal of solvent. The coacervation product deposits on the boundary layer of the material to be encapsulated with formation of a contiguous capsule wall and is solidified by drying or polymerization.

For enveloping solid core materials, mechanical-physical methods are suitable in which the envelope is formed in a fluid bed or by spray drying.

In the aforementioned boundary layer polymerization methods, the wall formation is realized by polycondensation or polyaddition of monomeric or oligomeric starting materials on the boundary layer of a water/oil emulsion.

In the case of adsorptive methods, layers of polyanionic and polycationic polymers are applied and form a capsule wall in this way which is usually comprised of 2 to 20 layers.

The employed polymers are preferably used in the form of their solutions, suspensions or emulsions. For the micro encapsulation aqueous solutions, suspensions, or emulsions of a concentration of 0.5 to 10% by weight were found to be suitable. As already mentioned above, one aspect of the invention is to immobilize vegetative microorganisms in such a way that they can be stored under life-supporting conditions over an extended period of time. In order to maintain the viability of the microorganisms, i.e., their activity, it is particularly preferred when culturing, and optionally the concentration and also the subsequent immobilization, are carried out under gentle conditions, in particular, under life-supporting conditions. In order to adjust the life-supporting conditions, it is preferred to supply the microorganisms during processing with substrate and oxygen. In order to obtain a functioning product as an end product which is usually supplied as such to the customer, it is particularly desirable when the aforementioned life-supporting conditions are maintained continuously, or at least almost continuously, during the manufacturing process and are also maintained during retail until reaching the hands of the customer.

For producing microcapsules from alginate, preferably a 1 to 5%, in particular, 1.5 to 2.5%, alginate suspension is used. This alginate suspension is mixed with the suspension of the microorganisms which preferably has a concentration as high as possible, and subsequently subjected to immobilization as is known in the art.

The manufactured immobilisates can be used without further processing steps such as drying. Drying of the obtained immobilisates for the purpose of storage is possible. They can be added as is known in the art to the water to be cleaned and/or treated. Preferably, the capsules are however introduced into a container which is installed fixedly within the water to be cleaned. It is also possible that the immobilisates, solely based on their specific weight, are stationary at a fixed location, i.e., they are not carried away by the current.

In an especially preferred embodiment, the obtained immobilisates are introduced into a filter and thus positionally secured by the surrounding filter material.

When being used in a body of water to be cleaned, the water flows through the filter unit and comes into contact with the immobilisate. Because of the preferably net-like structure of the matrix material, the material to be cleaned, including the harmful substances, penetrates into the interior of the immobilisate. The reaction of the immobilized microorganisms with the harmful substances cause the decomposition of the harmful substances. These substances which are harmful to the water act at the same time as nutrients for the microorganisms.

A further subject matter of the invention relates to the use of microorganisms in immobilized form for removal of harmful substances, such as nitrogen compounds and/or phosphate, from bodies of water and/or from the air.

A further subject matter of the present invention is a method for cleaning and/or treating bodies of water and/or soils by using living bacteria cultures which is characterized in that the vegetative microorganisms are present in immobilized form. The method according to the invention enables in particular removal of harmful inorganic and organic water ingredients such as nitrogen compounds and phosphate.

The immobilized microorganisms are stored before their use according to the invention preferably in an aerated and optionally cooled container in order to keep the possible activity loss as minimal as possible. In a preferred embodiment, this container is configured as a so-called dispenser from which the immobilisates can be removed in the desired quantity.

A further subject matter of the invention is a so-called kit-of-parts comprising an immobilized microbiological culture as described above as well as a container for receiving, storing and/or dispensing the culture under life-supporting conditions.

The enclosed FIG. 1 shows a schematic illustration of the biomass production for *Nitrosomonas* sp. as a pure culture in a bioreactor with biomass return. The culturing process is carried out in reactors with continuous flow through with biomass return by means of membrane filtration to final concentrations of $5 \times 10^8$ to $6 \times 10^9$ cells/ml. Culturing in fed-batch systems is also possible.

The invention claimed is:

1. A microbiological culture for triggering microbiological processes in artificial bodies of water, the microbiological culture comprising:

a bacteria mixture immobilized on a matrix, wherein the bacteria mixture comprises:
   a) ammonia-oxidizing bacteria;
   b) nitrite-oxidizing bacteria; and, optionally
   c) nitrate-reducing and nitrite-reducing bacteria;
wherein the matrix is selected from at least one polymer material selected from the group consisting of polymeric polysaccharides, proteins, ethyl cellulose, methylcellulose, carboxy methyl ethyl cellulose, cellulose acetate, alkali cellulose sulfate, polyanilline, polypyrrole, polyvinyl pyrrolidone, polystyrene, polyvinyl chloride, polyvinyl alcohol, polyethylene, polypropylene, copolymers of polystyrene and maleic acid anhydride, epoxy resins, polyethylene imines, copolymers of styrene and methyl methacrylate, polystyrene sulfonate, copolymers of polyacrylate and polymethacrylate, polycarbonate, polyester, silicones, methylcellulose, mixtures of gelatin and water glass, mixtures of gelatin and polyphosphate, mixtures of cellulose acetate and phthalate, mixtures of gelatin and copolymers of maleic acid anhydride and methyl vinyl ether, cellulose acetate butyrate, chitosan, poly dialkyl dimethyl ammonium chlorides, mixtures of polyacrylic acids and poly diallyl dimethyl ammonium chlorides, and suitable mixtures of the above;
wherein the ratio of cell numbers of ammonia-oxidizing bacteria to nitrite-oxidizing bacteria is in the range of 1:10,000 to 1:1; and wherein the ratio of nitrite-oxidizing bacteria to nitrate-reducing and nitrite-reducing bacteria is in the range of 1,000:1 to 1:1.

2. The microbiological culture according to claim 1, wherein the matrix is at least one member selected from the group consisting of a capsule, a gel, and a gel sphere.

3. The microbiological culture according to claim 2, wherein the matrix has a particle diameter of 1 μm to 10,000 μm.

4. The microbiological culture according to claim 3, wherein the particle diameter is 100 μm to 5,000 μm.

5. The microbiological culture according to claim 1, wherein the polymeric polysaccharides are at least one of agar-agar and cellulose, and wherein the proteins are at least one of gelatin, gum arabic, albumin, and fibrinogen.

6. The microbiological culture according to claim 2, wherein the matrix has a multi-layer configuration.

7. The microbiological culture according to claim 6, wherein the matrix material is selected from the group consisting of gel-forming polymers and film-forming polymers.

8. The microbiological culture according to claim 7, wherein the gel-forming polymers are selected from the group consisting of alginates and alginate derivatives, and wherein the film-forming polymers are selected from the group consisting of alkali cellulose sulfate, polyethylene imines and poly dialkyl dimethyl ammonium chlorides.

9. The microbiological culture according to claim 1, wherein the matrix further comprises phyllosilicates and tectosilicates added to the matrix material.

10. The microbiological culture according to claim 9, wherein the phyllosilicates and tectosilicates are zeolites.

11. The microbiological culture according to claim 1, wherein the ammonia-oxidizing bacteria and the nitrite-oxidizing bacteria are selected from the group consisting of *Nitrosomonas*, *Nitrosococcus*, *Nitrosospira*, *Nitrobacter*, and *Nitrosovibrio*; and the nitrate-reducing and nitrite-reducing bacteria are heterotrophic denitrification bacteria.

12. The microbiological culture according to claim 11, wherein: the ammonia-oxidizing bacteria and nitrite-oxidizing bacteria are selected from the group consisting of *Nitrosomonas halophilia*, *Nitrosomonas eutropha*, *Nitrosomonas europaea*, *Nitrosomonas oligotropha*, *Nitrosomonas ureae*, *Nitrosomonas aestuarli*, *Nitrosomonas marina*, *Nitrosomonas*, sp. 3 Nm 51, *Nitrosomonas communis*, *Nitrosomonas nitrosa*, *Nitrosomonas* sp. 1 Nm 33, *Nitrosomonas* sp. 2 Nm 41, *Nitrosomonas cryotolerans*, and *Nitrobacter winogradskyi*; and
   wherein the heterotrophic denitrification bacteria are selected from the group consisting of *Paracoccus* sp. and *Pseudomonas* sp.

13. The microbiological culture according to claim 1, wherein the bacteria are immobilized in the matrix material in the form of cell suspensions and wherein the concentration of the cell suspensions is between $5 \times 10^8$ to $6 \times 10^9$ cells/ml.

14. The microbiological culture according to claim 1, wherein the ammonia-oxidizing bacteria and the nitrite-oxidizing bacteria are each cultured in a pure culture.

15. The microbiological culture according to claim 1, wherein the ratio of cell numbers of ammonia-oxidizing bacteria to nitrite-oxidizing bacteria is in the range of 1:1,000 to 1:10, and the ratio of cell numbers of nitrite-oxidizing bacteria to nitrate-reducing and nitrite-reducing bacteria is in the range of 100:1 to 5:1.

16. The microbiological culture according to claim 2, wherein the matrix contains a buffer system selected from the group consisting of acetic acid/acetate, $HCO_3^-/CO_3^{2-}$, phosphoric acid/$H_2PO_3^-$/$HPO_3^{2-}$, $HSO_4^-$/$SO_4^{2-}$, citric acid/citrate, lactic acid/lactate, and solid $CaCO_3$.

17. A method for removing harmful substances from artificial bodies of water, the method comprising: adding an effective amount of the microbiological culture of claim 1 to the artificial bodies of water.

18. The method according to claim 17, wherein the harmful substances are at least one of phosphates, inorganic nitrogen compounds, and organic nitrogen compounds.

19. A kit comprising a microbiological culture according to claim 1 and a container for receiving and storing the microbiological culture under life-supporting conditions.

20. The microbiological culture according to claim 1, further comprising heterotrophic nitrification fungi and heterotrophic nitrification algae.

21. The microbiological culture according to claim 20, wherein the heterotrophic nitrification fungi are selected from the group consisting of *Aspergillus*, *Penicillium*, and *Cephalosporium*; and the heterotrophic nitrification algae are selected from the group consisting of *Arthrobacter* sp., *Alcaligenes faecalis* and *Nocardia* sp.

22. A microbiological culture according to claim 1 for triggering microbiological processes in aquariums, wherein the microbiological culture comprises a bacteria mixture comprising living chemo-lithoautotrophic bacteria and a matrix, wherein the bacteria mixture is immobilized on the matrix, wherein the bacteria mixture is comprised of:
   a) ammonia-oxidizing bacteria cultured in a pure culture;
   b) nitrite-oxidizing bacteria cultured in a pure culture; and optionally
   c) nitrate-reducing and nitrite-reducing bacteria;
wherein a ratio of cell numbers of a): b) is in the range of 1:10,000 to 1:1.

23. The microbiological culture according to claim 22, wherein said ratio of cell numbers of a): b) is in the range of 1:1,000 to 1:10.

* * * * *